United States Patent [19]

Nojiri et al.

[11] 4,230,806

[45] Oct. 28, 1980

[54] PROCESS FOR THE PRODUCTION OF MICROBIAL PROTEIN AND LIPID FROM VEGETABLE CARBOHYDRATES BY CULTURE OF MICROBES

[75] Inventors: Michihiko Nojiri, Takaishi; Kazuo Kakutani, Nishinomiya; Shigezo Uedono, Kigawahigashi; Kazuo Uenakai, Sakai; Masafumi Matsumoto, Shibatani, all of Japan

[73] Assignee: Mitsui Engineering & Shipbuilding Co., Ltd., Tokyo, Japan

[21] Appl. No.: 804,442

[22] Filed: Jun. 7, 1977

[51] Int. Cl.$^3$ .................................................. C10N 1/16
[52] U.S. Cl. ................................. 435/255; 435/42; 435/804; 435/813; 435/819
[58] Field of Search ................................. 195/13–16, 195/31 R, 82, 111, 115, 140, 141, 142, 88, 90; 435/255, 804, 42, 813, 819

[56] References Cited

U.S. PATENT DOCUMENTS

| | | | |
|---|---|---|---|
| 2,440,546 | 4/1948 | Jeffreys | 195/90 |
| 3,402,104 | 9/1968 | Gore et al. | 195/115 X |
| 3,630,848 | 12/1971 | Lefrancois | 195/109 |
| 3,868,307 | 2/1975 | Van Lanen et al. | 195/82 |
| 3,926,723 | 12/1975 | Green et al. | 195/101 X |
| 3,959,120 | 5/1976 | Pollock et al. | 195/141 |
| 3,979,522 | 9/1976 | Scott | 195/82 |
| 3,988,204 | 10/1976 | Andreasen et al. | 195/15 |
| 4,032,405 | 6/1977 | Tatsumi et al. | 195/82 |

*Primary Examiner*—Thomas G. Wiseman
*Attorney, Agent, or Firm*—Thomas E. Beall, Jr.

[57] ABSTRACT

A process for the production of microbial protein and lipid from vegetable carbohydrates including starch by culture of a microbe, which comprises a combination of the steps of liquefying starch with a dextrinogenic enzyme in a liquefaction tank, effecting simultaneous saccharification and culture of the microbe in a fermentation tank by aseptically adding a saccharogenic amylase to the culture medium produced in the liquefying step, and separating the cultured microbial cells and lipid from the culture medium.

11 Claims, 3 Drawing Figures

PROCESS FOR THE PRODUCTION OF MICROBIAL PROTEIN AND LIPID FROM VEGETABLE CARBOHYDRATES BY CULTURE OF MICROBES

BACKGROUND OF THE INVENTION

The present invention relates to a process for the production of microbial protein (referred to hereinafter sometimes as S.C.P.) and lipid from vegetable carbohydrates by culture of a microbe in a culture medium containing such carbohydrates. More particularly, the present invention relates to a process for the production of microbial protein and lipid from vegetable carbohydrates, especially starch, characterized by the two-step operation comprising liquefaction of starch by the action of dextrinogenic enzymes for preparing a culture medium for a microbe and saccharification of the liquified culture medium by aseptically adding a saccharogenic amylase to the culture medium while cultivating the microbe therein.

In recent years, single cell proteins are produced artificially from vegetable carbohydrates or mineral hydrocarbons by culturing a micro-organism. The proteins thus obtained originate from the cells of the cultivated micro-organism and are generally distinguished from those purely extracted from vegetable sources, such as beans, by a chemical means. These artificially produced proteins are useful as substitute for meat and find a wide variety of applications in food industry as substitute for meat, additives to foods and animal feeds, etc.

Hitherto, many studies have been reported on the production of S.C.P. from vegetable carbohydrates by culturing a microbe in a culture medium prepared from such carbohydrates. Used in these studies as starting material for fermentation or production of S.C.P. and lipid are carbohydrates represented typically by monosaccharides and oligosaccharides as well as starch, the latter being commercially available in a great quantity. Thus, the use of starch as starting material is desirable from the economical point of view. However, if a microbe used for culture can utilize only monosaccharides or oligosaccharides, starch or the like high molecular material must be previously hydrolyzed (saccharified) by some appropriate means before it is used for culture medium.

Typical conventional methods adopted for solving this problem are the so-called amylo process utilized for the production of alcohols from starch, the koji process and the election method between koji and amylo processes. According to these methods, koji (for example aspergillus oryzae) is cultured for several ten hours under suitable conditions in a preliminary step, preceding to the main fermentation process, whereby koji produces amylase which will be utilized for saccharification in the subsequent process. In this case, control and operation for the cultivation are complicated and the operation itself needs a prolonged period of time. Consequently, these methods are unsuited for such process as in the production of S.C.P. wherein a large amount of starting materials must be treated by a simple method within a short period of time.

Recently, the Symba process attracts public attention as a process for the production of S.C.P. from a waste water of starch processing. This process is a mixed culture (symbiotic) method wherein saccharification of thermally sterilized starch is carried out with a special kind of microbe (Endomycopsis fibligar) capable of producing amylase which is cultured in a separate fermentation tank in a main fermantation tank where the main yeast, *Candida utilis,* is cultured. However, if the initial concentration of the starch is high in the Symba process, a gelatinization phenomenon is surely expected to occur in the course of the thermal sterilizing treatment of the starch. It is surmised therefore that a limitation is inevitably established for the concentration of starch to be chrged into the process. As two different kinds of said yeasts are cultured together in the main fermentation tank, the well balanced growth between the two yeasts is taken up as a difficult problem. In addition, maintenance of the culture and the product of a stable quality is not easy in this process.

Under such circumstances, there is a great demand for development of a new process for producing S.C.P. from starch wherein culture of microbe is carried out easily and efficiently without any trouble.

BRIEF SUMMARY OF THE INVENTION

It is an object of the present invention to provide microbial protein useful as substitute for meat and additive to foods or animal feeds.

It is another object of the present invention to provide a process for the production of microbial protein and lipid from vegetable carbohydrates by culture of microbes.

It is still another object of the present invention to provide a process for the production of microbial protein and lipid by culture of microbes which comprises a step of liquefying starch by the action of a dextrinogenic enzyme thereon and a step of enzymatic saccharification of culture of the microbes.

It is further object of the present invention to provide a simple, automatically controlable process for the production of microbial protein and lipid wherein a large amount of starting material can be treated continuously and efficiently in a short period of time.

It is still further object of the present invention to provide a continuous multi-stage culture method for producing microbial protein wherein a differnce in level of pressure is maintained between individual culture tanks so as to control the amount of a flowing fermentation liquid between the individual culture tanks.

Other objects, features and advantages of the present invention will become apparent more fully from the following description.

DETAILED DESCRIPTION OF THE INVENTION

It has now been found that the disadvantages in the prior arts as described above can be overcome by establishing separately a step of enzymatic liquefaction of starch and a step of enzymatic saccharification and culture for effecting simultaneous enzymatic saccharification and culture of a microbe.

In accordance with the present invention, there is provided a process for the production of microbial protein and lipid from vegetable carbohydrates including starch by culture of a microbe, characterized by liquefying starch with a dextrinogenic enzyme in a liquefaction tank to prepare a culture medium for a microbe, effecting simultaneous enzymatic saccharification and culture of the microbe in a fermentation tank or tanks by aseptically adding a saccharogenic amylase to the culture medium while culturing the microbe therein, and separating the cultured microbial cells and lipid from the culture medium.

The process of the present invention involves as a whole an enzymatic liquefaction step for liquefying starch with a dextrinogenic enzyme to prepare a culture medium for a microbe, a sterilization step for the culture medium, an enzymatic saccharification and culture step for effecting simultaneous enzymatic saccharification and culture of the microbe in a fermentation tank of tanks by aseptically adding a saccharogenic amylase to the culture medium while culturing the microbe therein, a separation and concentration step for the cultured microbial cells, and a drying step for obtaining the desired microbial protein. The present invention is characterized in that the enzymatic liquefaction step is independent of the enzymatic saccharification and culture step.

Various kinds of high molecular carbohydrates and starch can be used as starting material for the present invention. The use of starch is preferred because it is commercially available in a great quantity at a low cost. Various vegetable starches such as potato starch and a waste liquor from a starch-manufacturing plant can be used as starting material.

When starch is used as starting material for the production of S.C.P., it must be hydrolyzed previously unless the microbe used has the amylase activity. Hydrolysis of starch is carried out continuously and rapidly by the aid of a commercially available dextrinogenic enzyme in the liquefaction step. Inorganic nutrient salts are then added to the hydrolyzed liquid until the concentration of the salts becomes optimal for culture of a microbe. Then, in the sterilization step, the culture medium thus prepared is sterilized by heat and is conveyed to a fermentation unit which consists usually of a series of several fermentation tanks. In the subsequent enzymatic saccharification and culture step, a commercially available saccharogenic amylase is added aseptically to the culture medium in the fermentation tanks where enzymatic saccharification and culture of the microbe are carried out simultaneously. In this manner the hydrolysis proceeds rapidly and effectively. It is well known that hydrolytic enzyme reactions such as saccharification are generally reversible and that a phenomenon of product inhibition occurs. In the process of this invention wherein saccharification and culture are carried out simultaneously, glucose or maltose liberated by the action of saccharogenic amylase is consumed successively by the coexisting microbe and thus quickly removed out of the hydrolytic reaction participation. Therefore, both the reverse reactions and the product inhibition become negligible. In fact, it requires 60–90 hours to saccharify independently a liquefied starch solution in a saccharifying reaction tank using a given amount of saccharogenic amylase until the degree of saccharification exceeds DE 97. Whereas, the time of batchwise culture of a Candida yeast was over 14–24 hours in the saccharification and culture step of this invention using a liquefied starch solution having a total sugar content of 4%. In the separation and concentration step, the cultured microbial cells are harvested, for example, by decantation and centrifugal separation. The microbial cells thus isolated are finally dried in the drying step whereby the desired microbial protein is obtained. The yield of the cultured microbial cells is 45–52% based on the amount of total sugar added and the amount of sugar remaining unused is 0.1–0.2%.

The present invention can more fully be understood from the following description taken in conjunction with the accompanying drawings in which.

Figure 1:
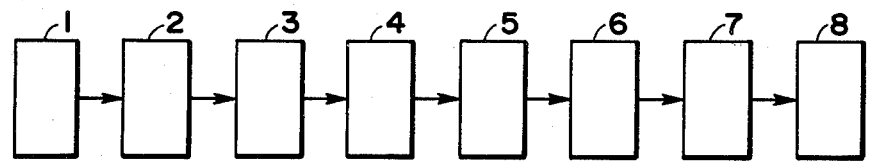
FIG. 1 is a flow sheet showing the steps of the process of this invention.

In FIG. 1, 1 is a preliminary step for preparing the starting material, 2 is an enzymatic liquefaction step for enzymatic hydrolysis of starch, 3 is a step for preparing a culture medium, 4 is a sterilization step by heating, 5 is enzymatic saccharification and culture step, 6 is a separation and concentration step for recovering the cultured microbial cells, 7 is a drying step, and 8 is the desired product.

In the preliminary step for preparing the starting material, various materials are treated according to the properties and forms of the materials thereby preventing any trouble in the subsequent steps. For example, if raw cassava or other similar kinds of raw potato roots are used as starting material, they must be ground, sieved and secondly ground, if necessary, and finally mixed with water to obtain desired concentration of starch. The pH value of the slurry is adjusted. If a waste liquor from a starch-manufacturing plant is used as starting material, a treatment for removal of protein is performed, if necessary, in addition to the essential treatments for adjustment of the pH value and the concentration of starch.

In the enzymatic liquefaction step, the properly prepared starting material is liquefied enzymatically by addition of a dextrinogenic enzyme ($\alpha$-amylase). This liquefied material is discharged continuously to two-stage liquefaction tanks and heated up to a temperature of 85°–88° C. A residence time is between 60 minutes and 90 minutes.

In the step for preparing a culture medium the liquefied material is diluted with water to form a solution having a total sugar concentration of 1–8%, usually 4%. Then, necessary amounts of inorganic nutrient salts containing nitrogen, phosphorus, magnesium and potassium are added to the medium and the pH value thereof is adjusted between 4.5 and 6. The existence of nitrogen source is necessary in the culture medium. One or more of inorganic compounds or sometimes organic nitrogen-containing compounds, such as urea, ammonium sulfate, ammonium phosphate and ammonium nitrate, are used as the nitrogen source in the culture medium. In addition, inorganic salts such as potassium dihydrogen phosphate, dissoium hydrogen phosphate, magnesium sulfate and ferrous sulfate are also added to the medium as other necessary nutrient source.

In the sterilization step, the culture medium thus adjusted is sterilized at 120°–135° C. under pressure for 10–60 minutes. This step is generally carried out continuously after preparation of the culture medium.

In the enzymatic saccharification and culture step, the sterilized culture medium is supplied to the fermentation tanks where yeasts, bacteria or other microorganisms are cultured. The use of yeasts belonging to Candida and Lipid-producing Rhodotorula, for example, *Candida utilis* and *Rhodotorula glutinis*, are preferred for the process of this invention. Simultaneously, a prescribed amount of the saccharogenic amylase (gluco-amylase) is also added aseptically to the tanks whereby the medium (liquefied solution) is saccharified and, at the same time, the microbes grow effectively using the produced glucose and maltose as carbon source. For adding the saccharogenic amylase aseptically, for example, a solution of saccharogenic amylase (such as Glucuzyme N solution, Amano Seiyaku KK, Japan) is sterilized by passing it through a microfilter with a pore size of about $0.2\mu$ (such as EX Millipore filter, Millipore Corp. U.S.A.) and then added to the medium. A culture is carried out under an aerobic condition conducted at a pH value of 4.0–7.0 and a temperature of 30°–45° C. with aeration and stirring. Although this step may be carried out batchwise, a continuous multi-stage culture can be used to achieve more efficient results. The continuous multi-stage culture is generally carried out using a fermentation unit having more than two fermentation tanks arranged serially.

Figure 2:
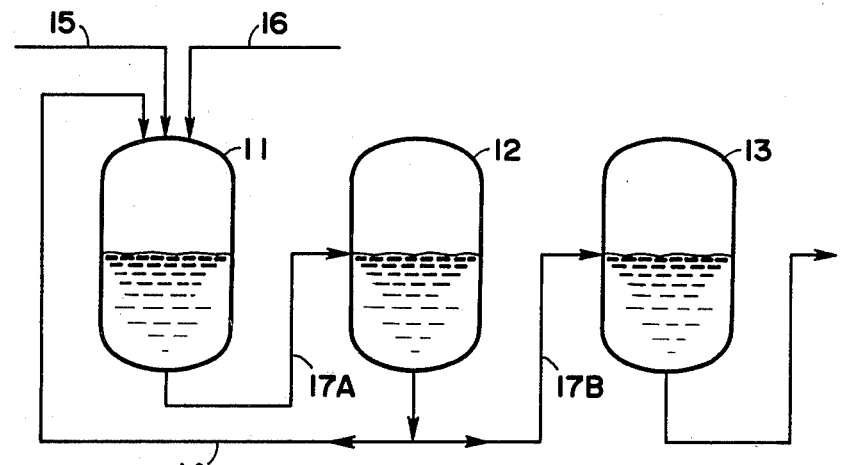
FIG. 2 is a schematic view showing one example for practicing the enzymatic saccharification and culture step.

In FIG. 2 showing one example of the enzymatic saccharification and culture step, such fermentation unit involves three fermentation tanks 11, 12 and 13 serially arranged. The volume of the third tank 13 is twice that of the first or second tank 11 or 12. The culture medium is fed through a pipe line 15 and the saccharogenic amylase through a pipe line 16. The three tanks are serially connected with two pipe lines 17A and 17B. A part of the culture medium is fed back from the second tank to the first tank through a pipe line 14, the amount of which is determined by the rate of growth of the microbe used, the effective capacity of the tanks, the concentration of the microbe, and the concentration and amount of the initial culture medium fed into the tanks.

The purpose of feeding back a part of the culture medium from the second tank to the first tank is to inoculate the first tank with the microbe with high growth rate in the second tank and thereby to stabilize the microbial concentration in the first tank so that the so-called washout phenomenon should not take place even if a larger amount of the culture medium is fed into the first tank. When the medium is fed bak in a continuous multi-stage culture operation, it is a general practice to feed back the medium from the last tank. However, the process of this invention is distinguished by feeding back the medium containing the microbe in logarithmic growth phase having high activity from the second tank.

In the continuous three-stage culture system of this example, therefore, increase in the microbial activity and promotion of saccharification are recognized in the first tank, the microbe in logarithmic growth phase exists and exhibits the maximum rate of growth in the second tank, and the microbe is in the so-called stationary phase in the third tank. The biological oxygen demand and the like value of the waste water of fermentation process are markedly minimized due to the microbial maturation and assimilation of remaining sugar in the last-stage tank.

Figure 3:
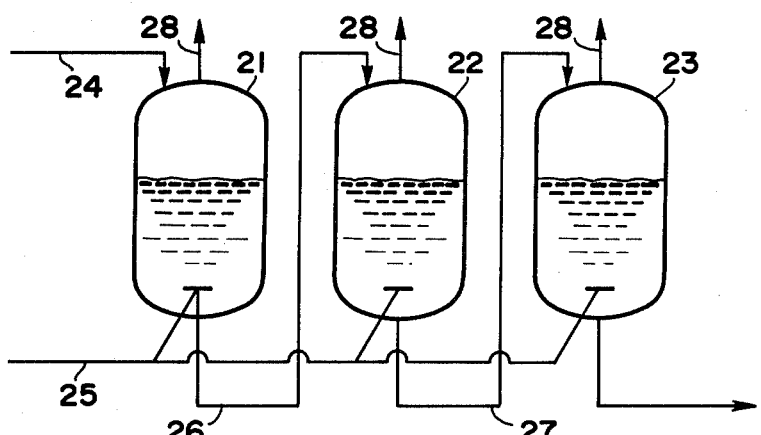
FIG. 3 is a schematic view showing another example for practicing the enzymatic saccharification and culture step.

In FIG. 3 showing another example of the anzymatic saccharification and culture step, the fermentation unit involves three fermentation tanks 21, 22 and 23 serially arranged as in the unit shown in FIG. 2 but is significantly improved in fermentation efficiency.

According to ordinary culture unit utilizing the so-called overflow system in the continuous multi-stage culture method, only the culture medium overflowing from one fermentation tank is carried over to the next fermentation tank. Hence, it is not so easy to keep the liquid level in the fermentation tank stable. As aeration is naturally indispensable to culture aerobic microorganisms, consequently liquid causes intense foaming. Furthermore, when molasses, waste starch solution or waste effluents from food industries are used as starting material for culture, foaming occurs violently due to various foaming components in such materials, whereby the flow of liquid from the first tank to the second tank or that from the second tank to the third tank accompanies foams or air bubbles which make the flow from tank to tank unstable. A consequent fluctuation in the flow rate and in the rate of dilution in the ordinary continuous methods of overflow or recycling system induces poor hold-up of microbial cells and undesirable reduction of the yield of products.

The fermentation unit of this example was devised to overcome the defects of the above mentioned feature and is characterized by maintaining a difference in level of pressure between the first, second and third fermentation tanks, thereby effecting continuous culture of aerobic microbes smoothly. Control of the liquid level becomes extremely difficult when the use of an easily foaming material causes a mixed emulsion of foams and liquids. According to this example, the liquid level in the tanks is well balanced because the flow of liquid is controlled by keeping a difference between pressure levels $P_1$ and $P_2$ of the tank 21 and 22, and $P_2$ and $P_3$ of the tank 22 and 23, respectively. If the liquid level in the first fermentation tank elevates due to violent foaming, the liquid level can be depressed by slightly increasing the pressure level $P_1$ while slightly increasing the pressure levels $P_2$ and $P_3$ as well, thereby enabling stable operation of continuous multistage culture.

In the continuous multi-stage fermentation unit involving the first tank 21, the second tank 22, and the third tank 23, which are connected through pipe lines 26 and 27, the starting material is fed through an inlet 24 into the first tank 21 and the air is supplied through a pipe line 25 into the individual tanks and exhausted through a vent 28. The flow rates in the individual tanks are well balanced by establishing a difference in level of pressure between the individual tanks in such manner that the pressure level is usually maintained at 1000–2500 mm Aq. in the first tank, at 600–1800 mm Aq. in the second tank and at 300–1500 mm Aq. in the third tank, whereby the liquid flows between the tanks through the pipe lines 26 and 27. If necessary, the pressure in the first tank may be elevated beyond 2500 mm Aq. When molasses, a waste starch solution, a waste effluent from food industries or the like containing foaming components is used as carbon source in culture of microbes, especially aerobic ones, aeration by dispersing air through the pipe line 25 as well as stirring of the medium by mechanical means is indispensable. In such case, the foaming becomes so violent that it may be impossible to continue the operation. According to the embodiment of this example, however, the liquid level can be controlled easily by establishing a difference in level of pressure between the individual tanks even such a condition. Further, slight elevation of the pressure in the tanks serves to increase the transfer rate of oxygen whereby the growth rate of aerobic microbes is enhanced to increase the yield. When a yeast belonging to Candida was continuously cultured in a medium containing inorganic nutrient salts and a carbon source prepared from agricultural products according to the improved fermentation unit shown in FIG. 3, the yield of S.C.P. was in fact 50% or more based on the fed substrate.

In the separation and concentration step for recovery of the cutured microbial cells, the culture medium in which growth of the microbe has been completed is subjected to decantation to separate the supernatant liquid from the microbial cells which were then concentrated. If necessary, the slurry of microbial cells are rinsed with water and concentrated again. This step is generally carried out using a nozzle type centrifugal separator or other types of separators such as decanters depending on the kind of the microbe used.

In the drying step a slurry or cake of the microbial cells is dried to prepare the end product. This drying treatment is usually carried out by using a spray dryer, a drum dryer or flash dryer. In some cases, a special type of dryer may be used for preparing the product in granular or pellet form.

According to the process of the present invention in which the enzymatic liquefaction step is carried out independently, the process can be operated as a simple chemical reaction as compared with the conventional method (such as Amylo process, koji process or Symba process) in which amylase producing microbes are to be cultured together prior to the main fermentation process. Accordingly, the present invention is advantageous in that a large amount of the starting material can be treated easily in a short period of time, that the operation is simple and may automatically be controlled, and that the starting material of a high concentration may be treated. Because enzymatic saccharification and culture of microbes can be carried out simultaneously, a container for saccharification can be omitted and hydrolysis proceeds more rapidly and efficiently. These merits are of particular importance for the large scale production of S.C.P.

The present invention will now be illustrated in more detail by way of examples.

EXAMPLE 1

Cassava roots (Tapioca) were ground and diluted with water to form a slurry having a starch content of approximate 16%. The pH value of the slurry was adjusted to 6.0-6.2 and a dextrigenic enzyme (Spitase K, Nagase Industrial Corp., Japan) was added in an amount of 0.2% based on the starch. This slurry was continuously liquefied at a temperature of 85°-88° C. in the enzymatic liquefying step. After removal of contaminates, the liquefied solution was diluted with water until the total sugar concentration in the solution became 1.5-6%. An appropriate amount of inorganic nutrient salts was added to the solution and the pH value thereof was adjusted to 4.5-5 whereby a culture medium was prepared. The culture medium was continuously sterilized by heat in a sterilizer and was then fed into first fermentation tank. In the enzymatic saccharification and culture step, Candida utilis was continuously cultured in the medium while adding the saccharogenic amylase continuously and aseptically to the medium at a given rate. Total time of the culture (residence time of the feed) was 4-8 hours. After centrifugal separation and concentration of the medium, the desired product, S.C.P., was obtained. The yield of the dry microbial cells was 45-53% based on the starch in tapioca.

EXAMPLE 2

Cassava roots (Tapioca) were treated and liquefied in the same manner as described in Example 1. The liquefied solution was diluted to have a concentration of 4% of starch. Necessary amount of inorganic salts such as inorganic compounds of nitrogen, phosphorous, potassium or the like, were added to the solution which was then sterilized by heat, and continuously fed into fermentation tank.

A yeast of Saccharomyces cerevisiae was continuously cultured in the culture medium while aseptically adding thereto 0.3 to 0.5% of saccharogenic enzyme based on the weight of total sugar in the medium. Enzymatic saccharification accompanying products of glucose and maltose and maltiplication of the yeast are simultaneously proceeded rapidly. Total time of the culture (residence time of the feed) was 6-10 hours. The culture of Saccharomyses cerevisiae which is usually fragile in a sugar solution can be carried out without any trouble even at a relatively high concentration of sugar such as several percent based on the substrates of the culture medium.

The yeast cells in the medium were separated, concentrated and dried whereby a mass of the dry yeast cells was obtained. The yield of the yeast cells was 45-50% based on the weight of starch in cassava roots.

EXAMPLE 3

A waste effluent from a potato starch plant (content of the dry matter: about 8%, content of a soluble nitrogen-free material: 3-4%) was adjusted to pH 6 and liquefied by adding thereto a given amount of the liquefying enzyme. Necessary inorganic nutrient salts were added to the solution to prepare a culture medium which was then sterilized by heat, and continuously fed into fermentation tank. A yeast belonging to Candida strain was continuously cultured in the medium while aseptically adding thereto saccharogenic amylase at a given rate. The yeast cells in the medium were separated, concentrated and dried whereby a mass of the dry yeast cells was obtained. In this case, it was estimated that about 45% of the soluble nitrogen-free material was converted into the yeast cells.

EXAMPLE 4

Raw cassava was treated and liquefied in the same manner as described in Example 1. The liquefied solution was diluted to have a total sugar concentration of 2-5%. Inorganic nutrient salts were then added to the solution to prepare a culture medium in which the C/N ratio of the nitrogen source was limited to 20-40.

The medium was sterilized and then fed into fermentation tank. A yeast belonging to Rhodotorula strain capable of producing lipid at a high rate was cultured either batchwise or continuously in the medium while aseptically adding thereto saccharogenic amylase at a given rate. After separation and condensation of the medium, the solid was dried to obtain dry yeast cells of a high lipid content. The yield of the dry yeast cells was 40-48% based on the starch in raw cassava. The lipid content in the dry yeast cells was 15-50%.

If a lipid extraction step is provided after the separation and condensation step for isolation of the yeast cells, a high quality lipid having a composition similar to that of a vegetable oil is obtained. Further, a dried residue after extraction of the lipid affords a dry mass of the yeast cells of high protein content.

EXAMPLE 5

Under the conditions as will be defined hereunder, continuous culture of a microbe was carried out using the fermentation unit shown in FIG. 3. The pressure was 1800 mm Aq. in the first tank, 1500 mm Aq. in the second tank and 1000 mm Aq. in the third tank. The amount of aeration was 0.5 VVM in the first tank, 1 VVM in the second tank and 0.5 VVM in the third tank. The total volumes of the first, second and third tanks were 500 l, 500 l 1000 l, respectively. The amount of culture medium was 300 l, 300 l and 600 l in the respective tanks and incubation of a microbe was carried out at feed rate of 250 l/hr. The microbe used was a yeast belonging to Candida genus. The culture medium used contained the following inorganic nutrient salts:

$NH_4NO_3$: 6 g
$KH_2PO_4$: 3 g
$Na_2HPO_4 \cdot 12H_2O$: 0.5 g
$MgSO_4 \cdot 7H_2O$: 0.5 g
$FeSO_4$: 0.5 g
Tap water: 1000 ml, pH 5.5

As a carbon source, a solution prepared by grinding, liquefying and saccharifying raw sweet potatoes was added as 4% glucose to the above culture medium. The pH value of the medium was adjusted with $NH_4OH$. As a result of this continuous three-stage culture, a period of the continuous culture was 500 hours, the yield was 50% or more based on the added carbon source, and the multiplication rate ($\mu$) of the yeast was 0.6.

EXAMPLE 6

The composition of the culture medium used was the same as described in Example 5. Molasses was added as a carbon source to the medium at a concentration of 4% (w/w) as sugar. *Candida utilis* was cultured continuously. The pressure levels in the first, second and third tanks were 2500 mm Aq. ($P_1$), 2,000 mm Aq. ($P_2$), and 1500 mm Aq. ($P_3$), respectively, and the amount of aeration was 1.0 VVM, 1.0 VVM and 0.5 VVM in respective tanks. The continuous three-stage culture method was carried out using the fermentation unit shown in FIG. 3. The size of the tanks and the amount of medium charged thereinto were identical with those in Example 5. As a result of this culture, the continuous culture of more than 300 hours was attained without any trouble by contamination with other microorganisms. The yield of the microbial cells was 52% based on the sugar concentration in the supplied molasses. No variation was observed in the microbial cells during the continuous culture.

EXAMPLE 7

An inorganic medium having the same composition as described in Example 5 was prepared and a waste solution of potato starch processing was used as a carbon source. *Candida utilis* was used as a yeast to be cultured in the medium. The carbon source was added to the medium at a concentration of 4%. The continuous culture was carried out under the same conditions as described in Example 6. The culture of the yeast could be continued for more than 400 hours without any trouble by contamination with other micro-organisms. The yield of the microbial cells was 48% based on the concentration of the added sugar. The protein content in the microbial cells was 46–52%.

EXAMPLE 8

Using molasses in place of candida utilis conventionally used as carbon source, *Rhodoturula glutinis* as a lipid-priducing yeast was cultured. The concentration of the carbon source was 4% (w/w). The inorganic medium was comprised of 75 mg/l of urea and 25 mg/l of $KH_2PO_4$ and was adjusted to have a pH value of 5.0. The amount of aeration was 0.5 VVM. A continuous culture of the yeast was carried out at a temperature of 32° C. with stirring at a speed of 200 rpm, using the fermentation unit shown in FIG. 3. The pressure levels in the first, second and third tanks were 1200 mm Aq. ($P_1$), 800 mm Aq. ($P_2$) and 500 mm Aq. ($P_3$), respectively. As a result of this continuous culture carried out for 250 hours, the lipid content reached 39.6% based on the dried yeast cell.

It is understood that the preceding representative examples may be varied within the scope of the present specification, both as to materials and culturing conditions, by one skilled in the art to achieve essentially the same results.

As many apparently widely different embodiments of this invnetion may be made without departing from the spirit and scope thereof, it is to be construed that this invention is not limited to the specific embodiments thereof except as defined in the appended claims.

What is claimed is:

1. A process for the production of protein and lipid from carbohydrates by culture of a yeast selected from the group consisting of the Candida strain and the Rhodotorula strain, comprising a first enzymatic step of liquefying the carbohydrate with a dextrinogenic enzyme to prepare a culture medium for the yeast, thereafter sterilizing said culture medium, thereafter a second enzymatic step of effecting simultaneous enzymatic saccharification and culture of said yeast by aseptically adding a saccharogenic amylase to said culture medium while culturing said yeast therein, and thereafter separating the cultured yeast cells and lipid from said culture medium.

2. A process according to claim 1 wherein said carbohydrate is starch.

3. A process according to claim 1 wherein said simultaneous enzymatic saccharification and culture of said microbe is effected by using a fermentation unit involving at least three fermentation tanks serially arranged.

4. A process according to claim 3 wherein a difference in level of pressure is maintained between individual fermentation tanks to control the amount of a flowing fermentation liquid between said tanks.

5. A process according to claim 1 wherein said yeast is *Candida utilis*.

6. A process according to claim 1 wherein said yeast is *Rhodoturula glutinis*.

7. A process according to claim 1 wherein inorganic nutrient salts are added to said culture medium.

8. A process according to claim 1 wherein said culture medium is sterilized at 120°–135° C. under greater than atmospheric pressure.

9. A process according to claim 1 wherein said cultured microbial cells are separated from said culture medium by centrifugal separation.

10. The process of claim 1 wherein said liquefaction is carried out at a temperature of up to 85°–88° C. and for 60–90 minutes, and saccharification is carried out at 30°–45° C.

11. A continuous multi-stage culture method for producing microbial protein, comprising:
  liquefying a carbohydrate to form a culture medium;
  thereafter sterilizing said culture medium to produce a sterilized culture medium;
  providing at least three culture tanks connected in series;

continuously introducing said sterilized culture medium, an amylase and a yeast culture into the first of said culture tanks to form a cultivation liquid;

continuously conducting the cultivation liquid from said first tank serially through the remainder of said culture tanks;

maintaining conditions suitable for yeast growth and saccharification of the carbohydrate in said first tank;

maintaining conditions suitable for logarithmic growth of said yeast in said second tank;

maintaining conditions suitable for stationary growth of said yeast in said third tank;

returning a portion of said cultivation liquid from said second tank to said first tank thereby maintaining the yeast concentration in the first tank at a desired level;

maintaining pressure of 1,000–2,500 mm. Aq. in the first of said tanks, 600–1,800 mm. Aq. in the second of said tanks, and 300–1,500 mm. Aq. in the third of said tanks to control the flow rates of the culture medium from tank to tank and the level of the culture medium in each tank within the desired range and to promote a spontaneous flow from tank to tank; and recovering microbial protein from the third tank.

* * * * *